(12) United States Patent
Goble

(10) Patent No.: US 6,336,926 B1
(45) Date of Patent: Jan. 8, 2002

(54) ELECTROSURGICAL SYSTEM

(75) Inventor: Nigel M Goble, Nr Cardiff (GB)

(73) Assignee: Gyrus Medical Limited, Wales (GB)

( * ) Notice: Subject to any disclaimer, the term of this patent is extended or adjusted under 35 U.S.C. 154(b) by 0 days.

(21) Appl. No.: 09/484,225

(22) Filed: Jan. 18, 2000

(30) Foreign Application Priority Data

Jan. 15, 1999 (GB) ............................................. 9900964

(51) Int. Cl.$^7$ ............................................. A61B 18/18
(52) U.S. Cl. ............................ 606/34; 606/41; 606/46; 606/48; 606/50
(58) Field of Search ............................ 606/1, 41–50, 606/93, 34; 604/174–180; 128/898

(56) References Cited

U.S. PATENT DOCUMENTS

| | | | |
|---|---|---|---|
| 4,202,337 A | | 5/1980 | Hren et al. |
| 4,381,007 A | | 4/1983 | Doss |
| 4,706,667 A | | 11/1987 | Roos |
| 5,403,311 A | | 4/1995 | Abele et al. |
| 5,776,106 A | * | 7/1998 | Matyas ........................ 604/180 |
| 5,810,809 A | | 9/1998 | Rydell |
| 5,813,409 A | | 9/1998 | Leahy et al. |
| 5,848,992 A | * | 12/1998 | Hart et al. ................... 604/167 |
| 5,882,341 A | * | 3/1999 | Bousquet ..................... 604/175 |
| 5,904,681 A | | 5/1999 | West, Jr. |
| 5,941,876 A | | 8/1999 | Nardella et al. |
| 6,102,046 A | * | 8/2000 | Weinstein et al. ........... 128/898 |
| 6,224,592 B1 | * | 5/2001 | Eggers et al. ................. 606/32 |

FOREIGN PATENT DOCUMENTS

| | | |
|---|---|---|
| EP | 0 754437 | 1/1997 |
| GB | 2017302 | 10/1979 |
| GB | 2308980 | 7/1997 |
| WO | WO 97/00646 | 1/1997 |
| WO | WO 97/00647 | 1/1997 |
| WO | WO 97/24993 | 7/1997 |
| WO | WO 97/24994 | 7/1997 |
| WO | WO 9748345 | 12/1997 |
| WO | WO 98/27880 | 7/1998 |
| WO | WO 99/29250 | 6/1999 |

* cited by examiner

Primary Examiner—Linda C. M. Dvorak
Assistant Examiner—David M. Ruddy
(74) Attorney, Agent, or Firm—Nixon & Vanderhye P.C.

(57) ABSTRACT

An electrosurgical system comprises a radio frequency generator (1), an electrosurgical instrument (E1), and a fluid enclosure (42). The generator (1) has a radio frequency output for delivery of power to the electrosurgical instrument (E1) when immersed in an electrically-conductive fluid. The electrosurgical instrument (E1) has an electrode assembly (32) at the distal end thereof, the electrode assembly comprising a tissue treatment electrode (34), and a return electrode (38) axially spaced therefrom in such a manner as to define, in use, a conductive fluid path that completes an electrical circuit between the tissue treatment electrode and the return electrode. The fluid enclosure (42) is adapted to surround an operation site on the skin of a patient or an incision leading to a cavity surgically created within the patient's body. The fluid enclosure (42) includes sealing means (44) for sealing against the patient's tissue, and the fluid enclosure includes at least one port (50*a*, 52*a*) through which the electrosurgical (E1) is insertable, and through which the electrically-conductive fluid can enter and/or leave the enclosure.

27 Claims, 11 Drawing Sheets

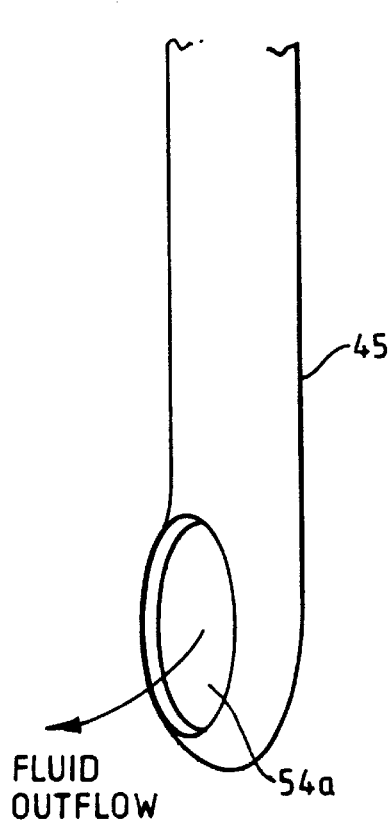
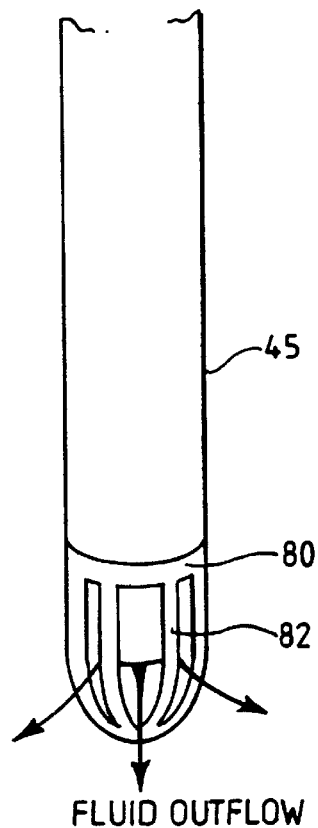
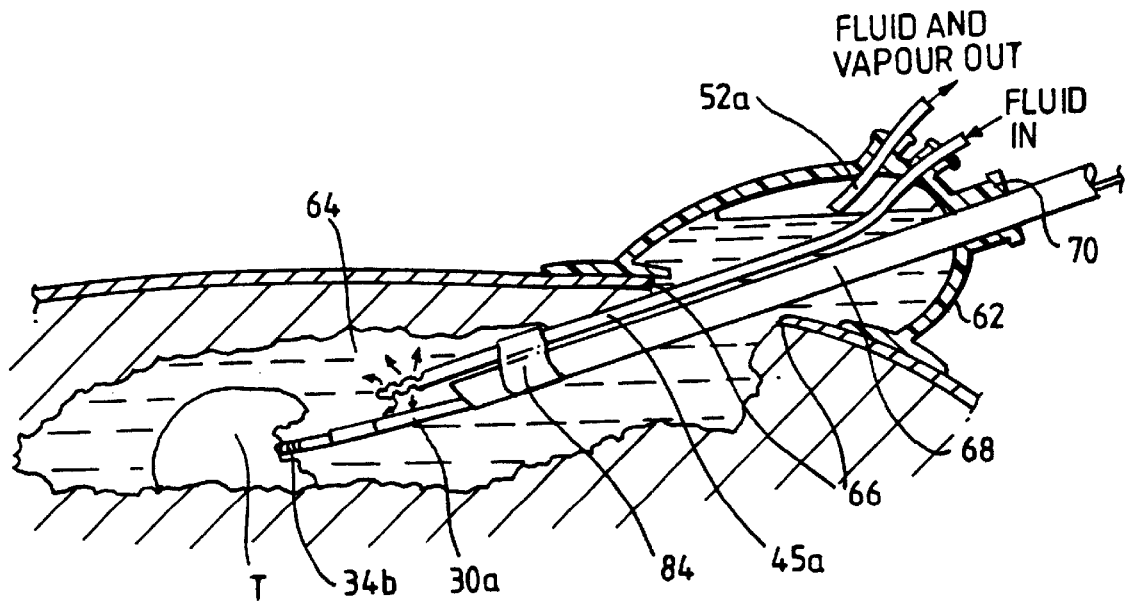

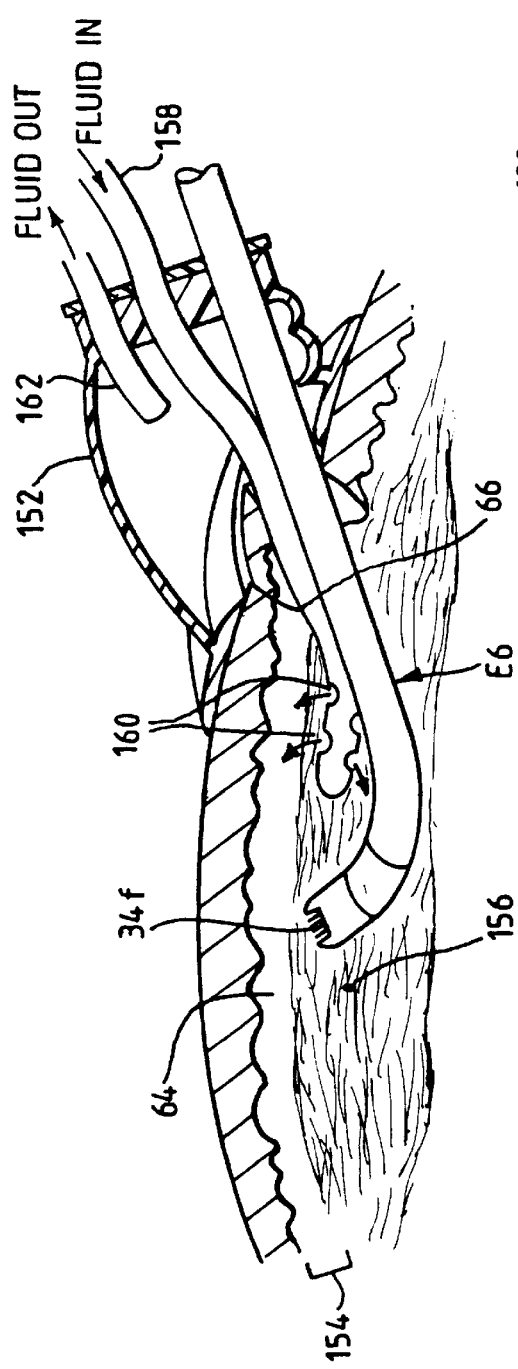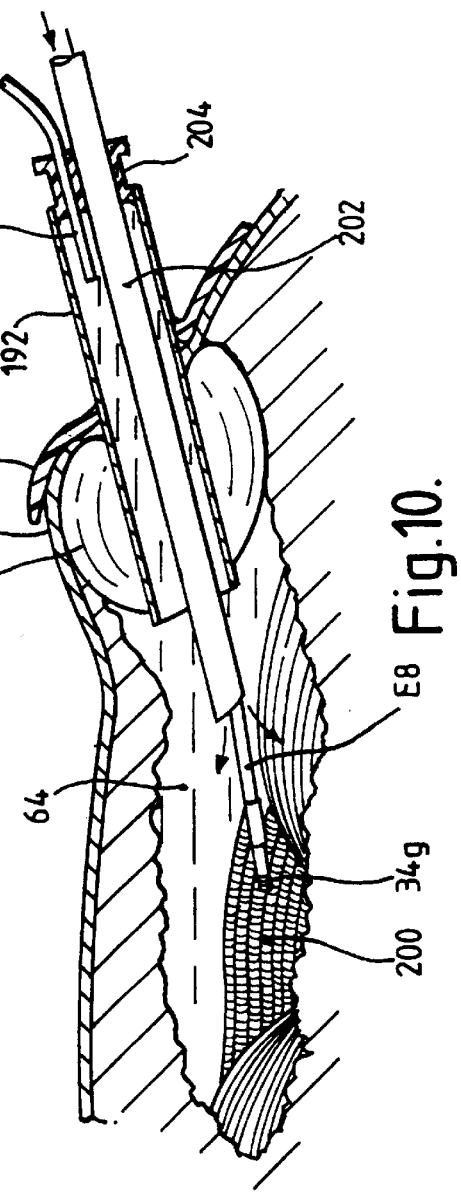

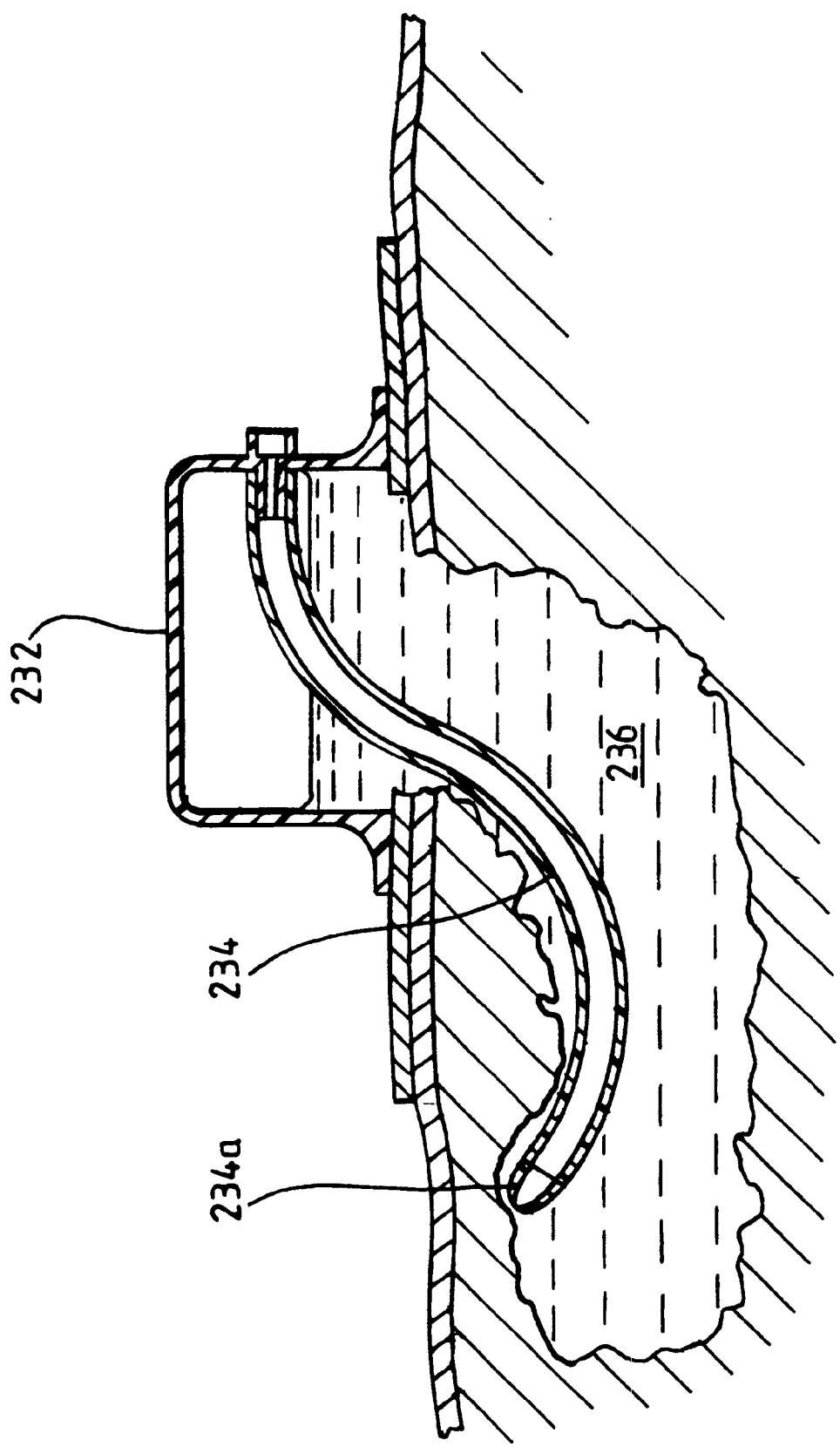

ELECTROSURGICAL SYSTEM

BACKGROUND TO THE INVENTION

This invention relates to an electrosurgical system for the treatment of tissue in the presence of an electrically-conductive fluid medium, and in particular to such a system including a fluid isolation enclosure for facilitating the immersion of tissues on, or within, a patient's body, such that the system can be operated to vaporise, coagulate, desiccate or otherwise thermally modify such tissues.

Endoscopic electrosurgery is useful for treating tissue in cavities of the body, and is normally performed in the presence of a distension medium. When the distension medium is a liquid, this is commonly referred to as underwater electrosurgery, this term denoting electrosurgery in which living tissue is treated using an electrosurgical instrument with a treatment electrode or electrodes immersed in liquid at the operation site.

Underwater surgery is commonly performed using endoscopic techniques, in which the endoscope itself may provide a conduit (commonly referred to as a working channel) for the passage of an electrode. Alternatively, the endoscope may be specifically adapted (as in a resectoscope) to include means for mounting an electrode, or the electrode may be introduced into a body cavity via a separate access means at an angle with respect to the endoscope—a technique commonly referred to as triangulation. These techniques are selected according to the nature, position and access to the body cavity to be treated.

When no such natural body cavity exists, one may be created using a variety of instruments or distensible balloons. This technique is used in such procedures as endoscopic saphenous vein harvesting, endoscopic extraperitoneal hernia repair, and where other subcutaneous tunnels are created to access and perform surgical procedures. Typically, the resulting pouch or cavity is not distended with fluid, and the procedure is conducted with instruments typical of those used to perform laparoscopic surgery (endoscopic surgery performed in the abdominal cavity). Laparoscopic surgery is also performed under gaseous or mechanical distension.

Electrosurgery is usually carried out using either a monopolar instrument or a bipolar instrument. With monopolar electrosurgery, an active electrode is used in the operating region, and a conductive return plate is secured to the patient's skin. With this arrangement, current passes from the active electrode through the patient's tissues to the external return plate. Since the patient represents a significant portion of the circuit, input power levels have to be high (typically 150 to 250 watts), to compensate for the resistive current limiting of the patient's tissues and, in the case of underwater electrosurgery, power losses due to the fluid medium which is rendered partially conductive by the presence of blood or other body fluids. Using high power with a monopolar arrangement is also hazardous, due to the tissue heating that occurs at the return plate, which can cause severe skin burns. There is also the risk of capacitive coupling between the instrument and patient tissues at the entry point into the body cavity.

With bipolar electrosurgery, a pair of electrodes (an active electrode and a return electrode) are used together at the tissue application site. This arrangement has advantages from the safety standpoint, due to the relative proximity of the two electrodes so that radio frequency currents are limited to the region between the electrodes. However, the depth of effect is directly related to the distance between the two electrodes; and, in applications requiring very small electrodes, the inter-electrode spacing becomes very small, thereby limiting tissue effect and output power. Spacing the electrodes further apart would often obscure vision of the application site, and would require a modification in surgical technique to ensure correct contact of both electrodes with tissue.

When either bipolar or monopolar electrosurgery is employed on the skin surface, there is a high risk of excessive thermal damage and tissue carbonisation. This is because the epidermis of the skin has a much higher electrical impedance than more vascular or moist tissues. Such thermal damage and carbonisation can lead to delayed healing, wound infection and excessive scar formation. In addition to these problems, when using bipolar arrangements, the impedance of the electrical contact between the skin and the return electrode can significantly reduce effectiveness. To overcome this problem, prior devices known in the art such as that of U.S. Pat. No. 4,202,337, use multiple arrangements of bipolar pairs in blade or needle-like electrode structures which penetrate the high impedance, superficial layers of the epidermis, such that one or more of the return electrodes makes adequate electrical contact with the tissue.

There have been a number of variations to the basic design of the bipolar probe. For example, U.S. Pat. No. 4,706,667 describes one of the fundamentals of the design, namely that the ratio of the contact areas of the return electrode and of the active electrode is greater than 7:1 and smaller than 20:1 for cutting or ablation purposes. When a bipolar instrument is used for desiccation or coagulation, for example as described in U.S. Pat. No. 5,403,311, the ratio of the contact areas of the two electrodes must be reduced to approximately 1:1 to avoid differential electrical stresses occurring at the contact between the tissue and the electrode (s).

The electrical junction between the return electrode and the tissue can be supported by wetting of the tissue by a conductive solution such as normal saline. This ensures that the surgical effect is limited to the active electrode, with the electric circuit between the two electrodes being completed by the tissue. One of the obvious limitations with such a design is that the active electrode (such as a needle) must be completely buried in the tissue to enable the return electrode to complete the circuit. Another problem is one of orientation: even a relatively small change in application angle from the ideal perpendicular contact with respect to the tissue surface, will change the contact area ratio, so that a surgical effect can occur in the tissue in contact with the return electrode.

Cavity distension provides space for gaining access to the operation site, to improve visualisation, and to allow for manipulation of instruments. In low volume body cavities, particularly where it is desirable to distend the cavity under higher pressure, liquid rather than gas is more commonly used due to better optical characteristics, and because it washes blood away from the operative site.

The applicants have found that it is possible to use a conductive liquid medium, such as normal saline, in underwater endoscopic electrosurgery in place of non-conductive, electrolyte-free solutions. Normal saline is the preferred distension medium in underwater endoscopic surgery when electrosurgery is not contemplated, or a non-electrical tissue effect such as laser treatment is being used. Although normal saline (0.9% w/v; 150 mmol/l) has an electrical conductivity somewhat greater than that of most body tissue, it has the advantage that displacement by absorption or extravasation from the operative site produces little physiological effect, and the so-called water intoxication effects of non-conductive, electrolyte-free solutions are avoided.

The applicants have developed a bipolar instrument suitable for underwater electrosurgery using a conductive liquid medium. Further details of the instrument and its operation are disclosed in the specification of our European patent application 96918768.1, the contents of which are incorporated herein by way of reference. Operation of this instrument requires that it is immersed in the electrically-conductive fluid, such that the fluid completes an electrical circuit between the two electrodes axially disposed on the shaft of the instrument. The instrument is connected to an electrosurgical generator of the type described in the specification of our European patent application 96304558.8, the contents of which are incorporated herein by way of reference, such that, in operation, the active or tissue treatment electrode of the instrument can produce vaporisation, coagulation, desiccation or thermal modification of tissue structures.

The requirement to immerse the instrument of 96918768.1 limits use to areas of the body which have natural boundaries such that a cavity is formed of dimensions and anatomical position suitable for distension with electrically-conductive liquid, for example in joints, the uterus, the bladder/urethra and the cranial cavity.

U.S. Pat. No. 4,381,007 describes the use of a rubber skirt which acts as a damming device for conductive coolant fluid used to bath the cornea of the eye. The purpose of the fluid is to support current flow between two or more electrodes arranged symmetrically and at prescribed distances from the cornea, such that the superficial surface is cooled, whilst tissues deep to the surface are treated sufficiently to correct refractive errors.

The practice of subcutaneous tunneling is also becoming common practice in order to create an artificial cavity in tissues for the purpose of performing endoscopic surgery. Typically, conventional bipolar or monopolar instruments are used, as these artificial cavities are not distended with fluid. These cavities are created between tissue planes using inflatable balloons or expandable blunt instruments through which an endoscope and instruments may be inserted.

The specification of our European patent application 97900315.9, the contents of which are incorporated herein by way of reference, describes an alternative embodiment of the instrument of 96918768.1 and an application of such an instrument to produce thermally-induced shrinkage of the pelvic floor as a corrective treatment of bladder neck descent.

SUMMARY OF THE INVENTION

The present invention provides an electrosurgical system comprising a radio frequency generator, an electrosurgical instrument, and a fluid enclosure, the generator having a radio frequency output for delivery of power to the electrosurgical instrument when immersed in an electrically-conductive fluid, the electrosurgical instrument having an electrode assembly at the distal end thereof, the electrode assembly comprising a tissue treatment electrode, and a return electrode axially spaced therefrom in such a manner as to define, in use, a conductive fluid path that completes an electrical circuit between the tissue treatment electrode and the return electrode, wherein the fluid enclosure is adapted to surround an operation site on the skin of a patient or an incision leading to a cavity surgically created within the patient's body, wherein the fluid enclosure includes sealing means for sealing against the patient's tissue, and wherein the fluid enclosure includes at least one port through which the electrosurgical instrument is insertable, and through which the electrically-conductive fluid can enter and/or leave the enclosure.

Advantageously, the fluid enclosure is provided with an inlet through which the electrosurgical instrument can be inserted, and preferably the fluid enclosure is provided with port means for supplying electrically-conductive fluid to, and removing said fluid from, the fluid enclosure. The fluid enclosure may be provided with a fluid inflow tube and a fluid outflow tube, each of which is associated with a respective port in the fluid enclosure. Conveniently, the fluid inflow tube is provided with a plurality of apertures at the distal end portion thereof.

Preferably, the inlet is adapted to receive an endoscope, the electrosurgical instrument being insertable, in use, through the endoscope. In this case, the fluid enclosure may be provided with a port through which electrically-conductive fluid can be removed from the enclosure, a working channel within the endoscope constituting a channel for delivering electrically-conductive fluid to the interior of the fluid enclosure.

In a preferred embodiment, the fluid enclosure is provided with a window, through which a surgeon can visualise the region surrounding the tissue treatment electrode. The window may be a magnifying window.

In one preferred arrangement, the electrosurgical instrument is a monopolar instrument having a single, tissue treatment electrode at the distal end thereof, and a metal collar positioned, in use, adjacent to the tissue treatment electrode constitutes the return electrode, the metal collar and the tissue treatment electrode being connected to the generator.

Advantageously, the fluid enclosure is such that it covers an area of skin surrounding the operation site or incision that is substantially larger than the area of the operation site or incision, whereby the volume of electrically-conductive fluid contained in the fluid enclosure is sufficiently large to ensure that its heat capacity is effective to remove heat away from tissue being treated.

In a preferred embodiment, the sealing means is constituted by an outwardly-extending flange provided on the fluid enclosure. Preferably, the flange is integrally formed with the fluid enclosure.

This fluid enclosure ensures that the electrosurgical instruments of any of the patent applications identified herein can be utilised on the surface of the body or anatomical structure to vaporise, coagulate, desiccate or thermally modify a variety of tissues.

Moreover, the fluid enclosure may be used to establish and maintain a fluidic distension of artificial cavities during use of such instruments to vaporise, coagulate, desiccate or thermally modify a variety of tissues.

In either case, the fluid enclosure may also include instrument access means to convert standard endoscopic dissection instruments, such that they can be utilised to desiccate or coagulate tissue structures utilising the generator described in the specification of our European patent application 96304558.8.

Our European patent application 96918768.1 relates to an electrosurgical instrument for producing thermally-induced shrinkage of the pelvic floor as a corrective treatment of bladder neck descent. The present invention provides access to the pelvic floor to facilitate one method of doing this.

The invention also provides a fluid enclosure device for use in -electrosurgical procedures, the device comprising a translucent flexible web member having a sealing flange at its periphery for forming a substantially fluid-tight seal with a patient's skin thereby to enable tissue to be treated within a substantially fluid-tight enclosure provided by the patient's skin and the flexible web member, and at least a first aperture in the web member to enable introduction of an electrosurgical instrument into the enclosure while maintaining integrity of the substantially fluid-tight seal.

Advantageously, the device further comprises a second aperture to enable supply of electrically-conductive fluid within the enclosure, a third aperture to enable removal of waste matter from within the enclosure, and a fluid outflow tube extending from the third aperture into the enclosure, the outflow tube being buoyant in electrically-conductive liquid.

The invention further provides a method of treating tissue using an electrosurgical system comprising an electrosurgical generator adapted to generate a radio frequency oscillating voltage output across first and second output terminals; an electrosurgical instrument having an active tissue treatment electrode connected to the first generator output terminal; fluid delivery means for delivering electrically-conductive fluid to the tissue to be treated; and a return electrode connected to the second generator output terminal, the method comprising the steps of: enclosing, in a substantially fluid-tight manner, a space within which the tissue to be treated is located, and within which at least the active electrode is located; operating the fluid delivery means at least partly to fill the space with electrically-conductive fluid; operating the generator to apply a radio frequency voltage between the active and return electrodes, and completing at least a part of a conduction path between the active and return electrodes using the electrically-conductive fluid; and manipulating the active electrode in the vicinity of the tissue to be treated.

Advantageously, the method further comprises the step of positioning the return electrode within the space.

Preferably, the electrosurgical instrument comprises a shaft, and the active and return electrodes are located on a distal end of the shaft, the method further comprising the steps of positioning the proximal end of the shaft to extend out of the space, and manipulating the active electrode by moving the proximal end of the shaft.

Conveniently, electrically-conductive fluid is supplied to the space continually, and the method further comprises the step of removing waste matter from within the space.

The space may be enclosed by means of a flexible enclosing member which forms a seal with a patient's skin, and the method further comprises the step of reducing the pressure within the space to a level below air pressure in the immediate vicinity outside the space. Alternatively, the space may be enclosed by means of a flexible enclosing member which forms a seal with a patient's skin, and the method further comprises the step of adhesively fixing the flexible member to the patient's skin.

Preferably, the enclosing step is such that the space encloses a region of the epidermis. In this case, the active electrode may be manipulated to achieve at least one of the following: treatment of skin lesions; removal of tumours; dermabrasion; reduction of wrinkles; removal of wrinkles; treatment of solar keratosis; treatment of basal cell carcinoma.

Alternatively, the enclosing step is such that the space encloses a cavity within which the tissue to be treated is situated. The cavity may be a natural body cavity. In this case, the active electrode may be manipulated to achieve at least one of the following: thermal modification of collagen fibres, treatment of parenchyma and mesanchymal tumours. The thermal modification of collagen fibres may be performed to correct bladder neck descent or to treat ligaments or tendons.

One advantage of the invention is that immersion of tissue structures, such as skin, in the electrically-conductive fluid, reduces the impedance of the electrosurgical output, such that skin surfaces can be cut, vaporised, contoured (cutaneous thermabrasion) or otherwise thermally modified, whilst minimising char formation and undesirable thermal damage to tissue margins. This is particularly advantageous when debriding wounds or ulcers, and in the treatment of a variety of cutaneous or dermatological disorders. Such disorders include: malignant tumours (whether primarily or secondarily involving the skin); port wine stains; telangiectasia; granulomas; adenomas; haemangioma; pigmented lesions; nevi; hyperplastic, proliferative and inflammatory fibrous papules; rhinophyma; seborrhoeic keratoses; lymphocytoma; angiofibromata; warts; neurofibromas; condylomata; keloid or hypertrophic scar tissue.

Another advantage of the invention is that the desiccation capability is considerably improved by the immersion of structures in the electrically-conductive fluid, particularly as it applies to simple probe type devices such as hooks. This is a result of several factors. The first of these relates to the fact that tissue surfaces dry out quite quickly during surgical procedures, which increases the impedance of electrical contact with tissues. As desiccation performance is current-driven, the high impedance prevents adequate current delivery, and the output impedance of a desiccate voltage range is exceeded. As a result, the tissue is incompletely desiccated and, if this occurs during desiccation of a blood vessel, the lumen will still be patent and any bleeding will not be controlled. The second of these factors occurs as a result of this high impedance tissue adhering to the surface of the tissue treatment electrode. This compounds the problem, as it further reduces the effectiveness of desiccation. The third is that both these factors are enhanced when the tissue treatment electrode has a small contact surface area, particularly if this electrode is a hook which has been used for cutting, as this leads to carbonisation and pitting of the electrode surface, prior to use as a desiccating instrument. These disadvantages are overcome by use of the present invention. In particular, the improved desiccation performance is useful when sealing venous or thin-walled vascular structures as may be encountered during treatment of haemangioma, varicosities or other vascular anomalies as well as during venous harvesting.

Yet a further advantage of the present invention is that the irrigation of artificial cavities with an electrically-conductive or physiological solution, such as normal saline, provides a number of benefits. The surfaces of tissues exposed during the procedure are prevented from dehydrating, thereby improving their viability, particularly when the healing process is initiated. Tissue debris, electrosurgical smoke and blood are washed from the operative site so improving visualisation. Such devascularised debris produces tissue reactions which could potentially delay healing, increase post-operative pain associated with inflammatory mediators, and increase the risk of wound infection. The consistency of electrical performance of the invention is improved by immersion of the operative site in an electrically-conductive liquid, whereby the voltage potential required to initiate an arc in vapour is more constant compared to the variable effects of different gaseous environments on arc potential.

Still another advantage of the present invention is in providing tunnelled access to tissue structures for which, when immersed in an electrically-conductive fluid, the desiccation function can be utilised thermally to modify these structures. Such access techniques can be used to modify collagen-containing tissues which have become lax for a variety of reasons. The laxity of support ligaments is a common cause for prolapse or descent of structures which, when not supported correctly, commonly do not function correctly. An example of such a situation is bladder neck descent in women, wherein the closure mechanism of the bladder becomes ineffective under conditions of stress, such as straining, coughing or physical activity. The ligaments of the bladder neck and pelvic floor could be accessed by tunneling through the perineum to create a working cavity adjacent to these support structures. Such a cavity can then be distended by utilising the present invention for the purposes of modifying these support structures.

BRIEF DESCRIPTION OF THE DRAWINGS

The invention will now be described in greater detail, by way of example, with reference to the drawings, in which:

FIGS. 4a to 4d show alternative fluid delivery/evacuation arrangements for use with the first and second embodiments;

FIGS. 8 and 9 are diagrammatic representations of modified forms of the second embodiment;

FIG. 10 is a diagrammatic representation showing an alternative sealing means for use with any of the forms of the second embodiment;

FIGS. 13a to 13d show modified arrangements utilising a fluid outlet tube having a floating tip.

DESCRIPTION OF PREFERRED
EMBODIMENTS

Figure 1:
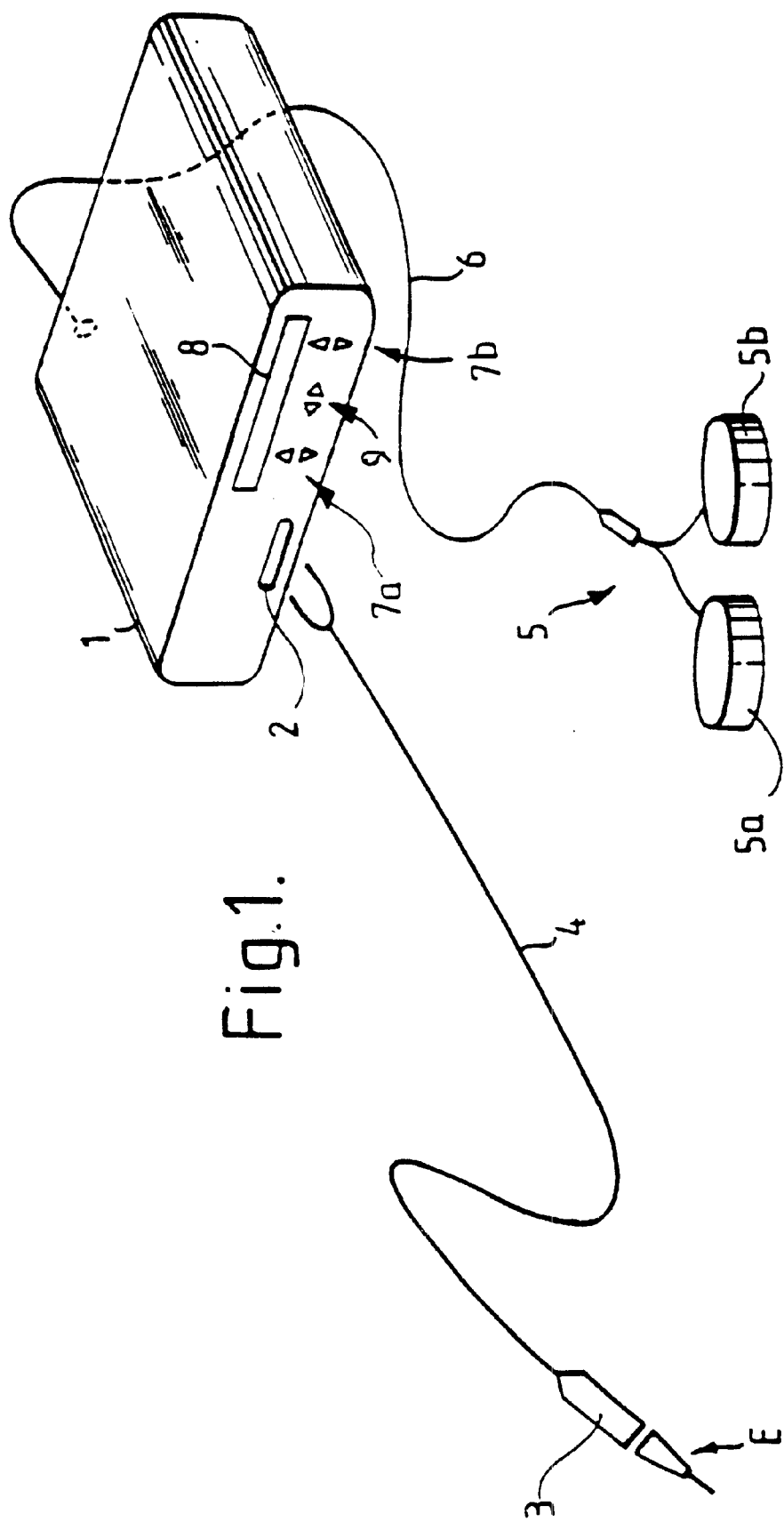
FIG. 1 is a diagram showing an electrosurgical apparatus forming part of the electrosurgical system of the invention.

Referring to the drawings, FIG. 1 shows electrosurgical apparatus including a generator 1 having an output socket 2 providing an RF output for an instrument in the form of a handpiece 3 via a connection cord 4. Activation of the generator 1 may be performed from the handpiece 3 via a control connection in the cord 4, or by means of a footswitch unit 5, as shown, connected separately to the rear of the generator 1 by a footswitch connection cord 6. In the illustrated embodiment, the footswitch unit 5 has two footswitches 5a and 5b for selecting a desiccation mode and a vaporisation mode of the generator 1 respectively. The generator front panel has push buttons 7a and 7b for respectively setting desiccation and vaporisation power levels, which are indicated in a display 8. Push buttons 9a are provided as an alternative means for selection between the desiccation and vaporisation modes. The electrosurgical apparatus forms part of an electrosurgical system which can be used for vaporising, cutting, contouring, desiccating, coagulating or otherwise thermally modifying tissue structures on the surface of or close to, the surface of a patient's body. The generator 1 is described in greater detail in the specification of our European patent application 96304558.8.

The handpiece 3 mounts a detachable electrode unit E, such as the electrode units E1 to E9 to be described below. Other electrode units that can be used with the invention are described in the specifications of our European patent application 96918768.1, British patent application 9600352.0, European patent application 97900315.9, European patent application 97926141.9, European patent application 96918767.3 and European patent application 97900314.2, the contents of which are incorporated herein by way of reference. Alternatively, the electrosurgical instrument may include, instead of the handpiece 3, a connector in the form of a one-piece electrode assembly.

Figure 2:
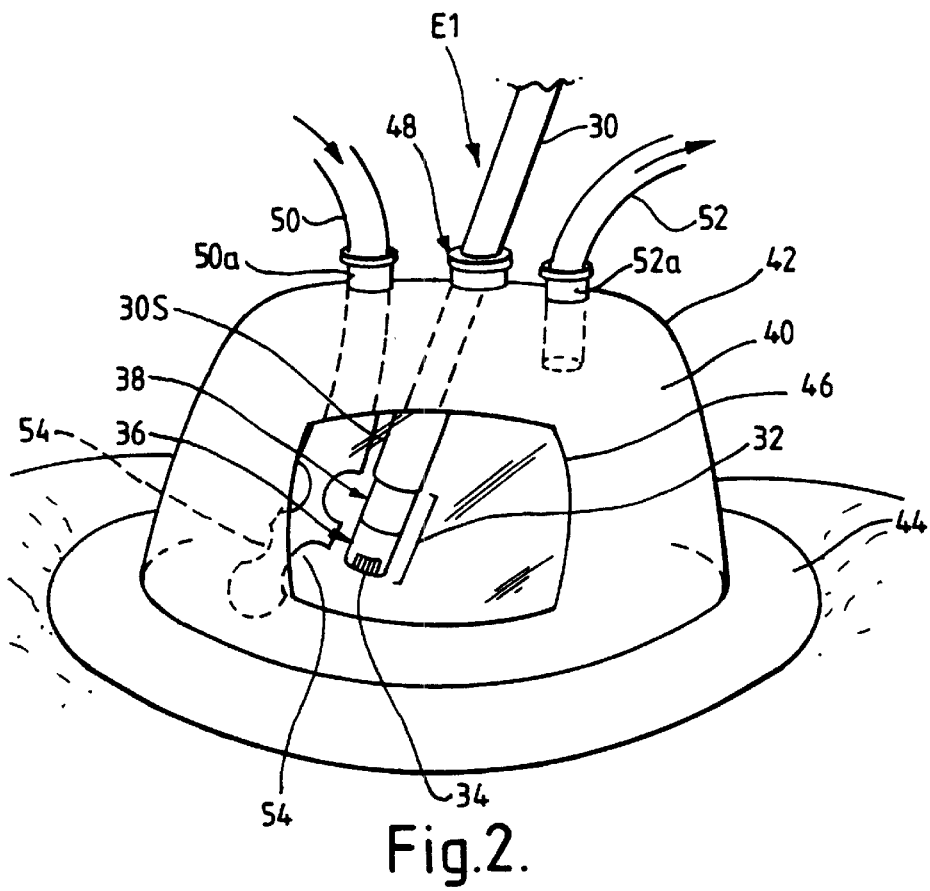
FIG. 2 is a diagrammatic representation, on a larger scale, of a fluid isolation enclosure and an electrode unit of a first embodiment.

In a first embodiment, shown in FIG. 2, an electrode unit E1 is detachably fastened to the handpiece 3 (not shown). The electrode unit E1 comprises a shaft 30 which may be a conductive (e.g. metallic) tube covered with an insulating sheath 30S, with an electrode assembly 32 at the distal end of the shaft. At the other end of the shaft 30 (not shown), means are provided for connecting the unit E1 to the handpiece 3 both mechanically and electrically.

The electrode assembly 32 is bipolar, having an active (tissue treatment electrode) 34 which is axially spaced from a return electrode 38 by means of an insulator 36. The return electrode 38 is constituted by the distal end portion of the tube 30, the portion not being covered by insulating sheet material. In use, the active electrode 32 is positioned in contact with, or in close proximity to, the tissue to be treated. This means that, in normal use when the electrode assembly 32 is immersed in a conductive fluid medium 40, the return electrode 38 remains spaced from the tissue being treated by the insulator 36, and a current path exists between the two electrodes through the conductive fluid contained within an enclosure 42.

To facilitate use of the electrode assembly 32 on the surface of a patient's body, the fluid enclosure 42 is affixed to the surface of the body, to provide a fluid seal, by means of adhesive fixing and sealing means constituted by a flange 44 as shown in FIG. 2. The enclosure 42 is formed with a magnifying window 46 provided in a side wall. The electrode unit E1 can be introduced into the fluid 40 through a port 48 provided in the enclosure 42. More than one port 48 may be provided for simultaneous use of more than one instrument, or for use of an instrument/endoscope combination, wherein the technique of triangulation is employed.

The enclosure 42 is provided with a fluid inflow tube 50 for delivering conductive fluid (such as saline) via a standard fluid injection delivery system (not shown), which system commonly includes a fluid bag and a tubing set. Advantageously, the exit from the fluid inflow tube 50 is positioned in close proximity to the tissue surface to be treated, so that tissue debris and/or blood is removed from the operation site. The enclosure 42 is also provided with a fluid outflow tube 52 positioned at the top of the enclosure, such that bubbles of vapour produced during use are preferentially dispelled from the enclosure. To facilitate removal of vapour, the outflow tube 52, is connected to a conventional vacuum pump (not shown). Additionally, the outflow and inflow may be balanced using an integral inflow and outflow pump. The tubes 50 and 52 enter and leave the enclosure 42 via respective ports 50a and 52a.

If the fluid enclosure 42 is a flexible bag, using a vacuum pump will collapse the bag, which is obviously undesirable. If, however, the fluid enclosure 12 is a rigid structure, then a vacuum pump may be desirable, as it will secure the enclosure to the tissue surface. A flexible enclosure would require positive pressure. Restriction of flow would, then, need to occur at the outlet. There will, in any case, be a danger of a siphon effect, which could cause similar problems as the vacuum pump. The siphon effect can be prevented by an air bleed such s a gas-permaeable membrane.

A further advantage is achieved by providing a diffuse delivery of fluid through a number of apertures 54 in the tube 50, rather than using a single delivery orifice. This overcomes the effects of fluid flow which, when directed at the tissue treatment electrode 34, increases the power required to exceed the vaporisation threshold, shown as point C in FIG. 12, the aspects of which are further described below.

Figure 3:
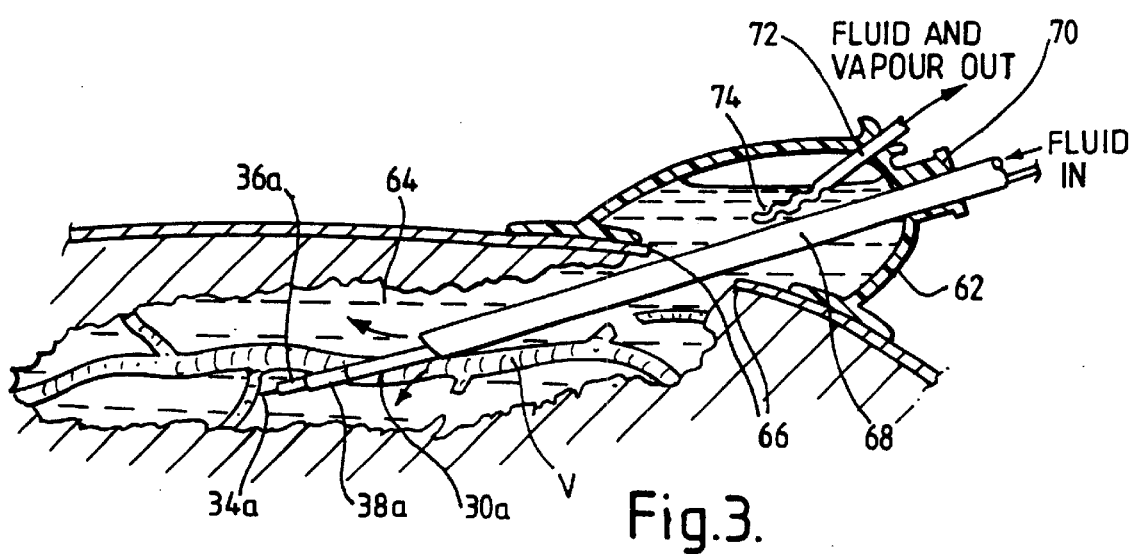
FIG. 3 is a diagrammatic representation of a second embodiment of a fluid isolation enclosure and an electrode unit.

In a second embodiment, shown in FIG. 3, a fluid enclosure 62 is positioned over a site on the patient's body wherein a space 64 has been surgically created in the tissues through an incision 66. This space 64 may be created using a dissecting instrument under endoscopic visualisation prior to application of the fluid enclosure 62, or may be created under a fluid-filled environment using an electrosurgical instrument or instruments based on the electrode assembly 32, or may be based on a combination of the two. Advantageously, the fluid-filled environment, combined with the generator 1 and instrument system for use with the invention, allows the use of tissue treatment electrodes commonly used for dissection, for example, the hook electrode 34a shown in FIG. 3 or a needle electrode. Such electrodes allow the sealing of larger blood vessels than would normally be treated in this way in a gaseous environment. This is particularly beneficial when sealing, for example a large vein such as that shown at V in FIG. 3, during subcutaneous vein harvesting, or as part of the treatment of varicosities.

The electrosurgical instrument of this embodiment is used in conjunction with a resectoscope 68 which is inserted through a port 70 in the enclosure 62. In this example, a conductive fluid (such as saline) is introduced through a fluid delivery channel of the endoscope 68. The fluid may alternatively be delivered through a dedicated inflow tube (not shown). In the illustrated example of FIG. 3, the electrosurgical instrument includes an electrode unit E2 including the active electrode 34a, a return electrode 38a constituted by the uncoated distal end of the metallic instrument shaft 30a, and an insulator 36a axially separating the two electrodes. The instrument is inserted through the working channel of the endoscope 68. Alternatively, the instrument my be inserted through a separate port in the enclosure 62, or via a second incision and second enclosure (not shown) positioned to access the same tissue cavity 64. The fluid outflow is provided by holes 74 in an outflow tube 72.

Figure 12:
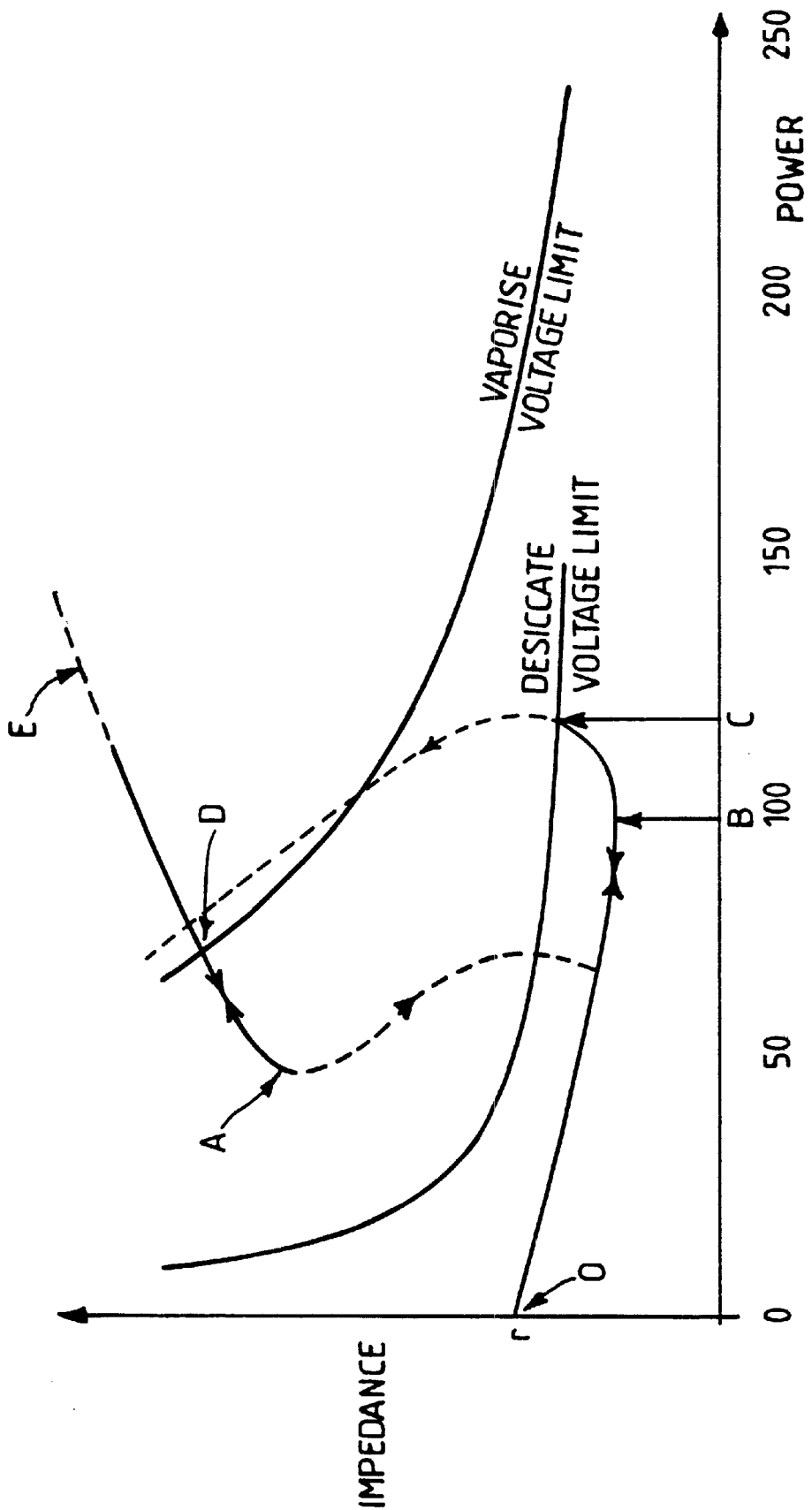
FIG. 12 is a graph illustrating the hysteresis of the electrical load impedance and the dissipated radio frequency (RF) power which occurs during use of a bipolar electrode unit used with the invention in desiccating and vaporising modes.
Figure 13A:
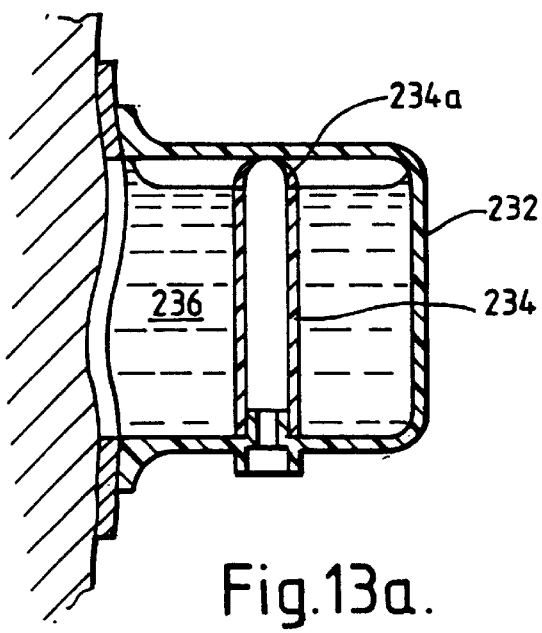
Figure 13B:
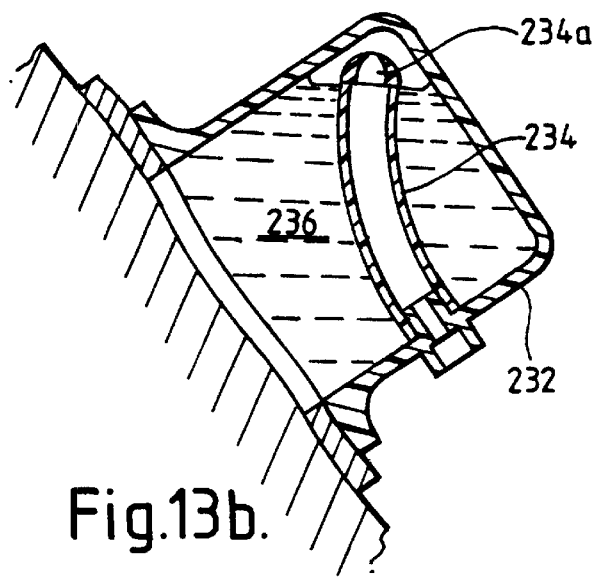
Figure 13C:
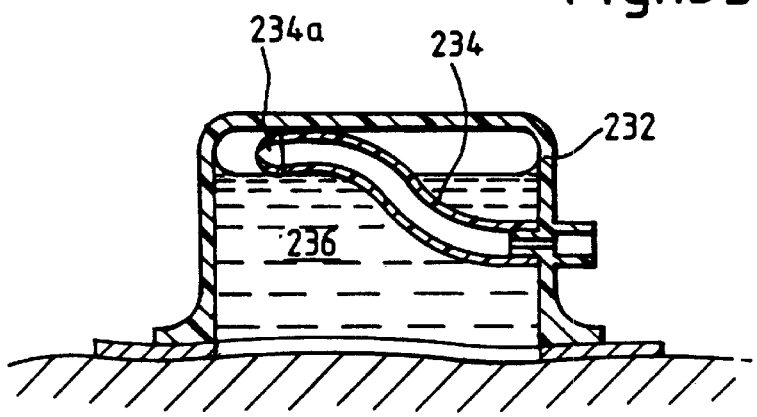

When used in combination with the electrosurgical generator 1 of FIG. 1, the electrode unit E1 of FIG. 2 (or the electrode unit E2 of FIG. 3) can be employed in the conductive fluid medium (saline) for tissue removal by cutting or vaporisation, for sculpting and contouring menisci for vaporisation, coagulation, desiccation or other thermal modification of tissue on, or within, a patient's body, or for desiccation, depending on the manner in which the generator is controlled. FIG. 12 illustrates how the generator 1 can be controlled to take advantage of the hysteresis which exists between the desiccation and the vaporising modes of the electrode unit E1. Thus, assuming the electrode assembly 32 of the unit E1 is immersed in a conductive medium such as saline, there is an initial load impedance "r" at point "O", the magnitude of which is defined by the geometry of the electrode assembly and the electrical conductivity of the fluid medium. The value of "r" changes when the active electrode 34 or 34a contacts tissue, the higher the value of "r" the greater is the propensity of the electrode assembly 32 to enter the vaporisation mode. When RF power is applied to the electrode assembly 32, the fluid medium heats up. Assuming the fluid medium is normal saline (0.9% w/v), the temperature coefficient of conductivity of the fluid medium is positive, so that the corresponding impedance coefficient is negative. Thus, as power is applied, the impedance initially falls and continues to fall with increasing power dissipation to point "B", at which point the saline in intimate contact with the electrode assembly 32 reaches its boiling point. Small vapour bubbles form on the surface of the active electrode 34 or 34a, and the impedance then starts to rise. After point "B", as power dissipation is increased further, the positive power coefficient of impedance is dominant, so small increases in power now bring about large increases in impedance.

As a vapour pocket forms from the vapour bubbles, there is an increase in the power density at the residual electrode/saline interface. There is, however, an exposed area of the active electrode 34 or 34a not covered by vapour bubbles, and this further stresses the interface, producing more vapour bubbles and thus even higher power density. This is a run-away condition, with an equilibrium point only occurring once the electrode is completely enveloped in vapour. The only means of preventing the run-away condition is to limit applied voltage, thereby preventing power dissipation into higher impedance loads. For given set of variables, there is power threshold before this new equilibrium can be reached (point "C").

The region of the graph between the points "B" and "C", therefore, represents the upper limit of the desiccation mode. The transition from point "C" to the vaporise equilibrium state will follow the power impedance curve for the RF stage of the generator 1 (shown as a dotted line in FIG. 12). Once in the vaporisation equilibrium state, the impedance rapidly increases to around 1000 ohms, with the absolute value depending on the system variables. The vapour pocket is then sustained by discharges across the vapour pocket between the active electrode 34 or 34a and the vapour/saline interface. The majority of power dissipation occurs within this pocket, with consequent heating of the active electrode 34 or 34a. The amount of energy dissipation, and the size of the pocket, depends on the output voltage. If this is too low, the pocket will not be sustained; and, if it is too high, the electrode assembly 32 will be destroyed. It should be noted that, if power were delivered at the same level as point "C", the resulting voltages would cause electrode destruction. The normal operating point for an electrode used for vaporisation is illustrated by point "D". This point is defined uniquely by the combination of the impedance power characteristic for the electrode in conjunction with the vaporise voltage limit. The dotted line E indicates the power level above which electrode destruction is inevitable As the power is reduced, the impedance falls until, at point "A", the vapour pocket collapses an the electrode assembly 32 reverts to the desiccation mode. At this point, power dissipation within the vapour pocket is insufficient to sustain it, so that direct contact between the active electrode 34 or 34a and the saline is re-established, and the impedance falls dramatically. The power density at the active electrode 34 or 34a also falls, so that the temperature of the saline falls below boiling point. The electrode assembly 32 is then in a stable desiccation mode.

Generator power control to achieve the required desiccation, tissue cutting and vaporisation functions is carried out by sensing the peak RF voltage appearing across the output connections of the generator 1, and by rapidly reducing the delivered output power whenever a preselected peak voltage threshold is reached. In a desiccation mode at least, this power reduction is significantly more than that required merely to bring the peak output voltage below the threshold. Preferably the power reduction is at least 50% to take advantage of the hysteresis characteristic described above with reference to FIG. 12.

During use of fluid irrigation, directing the fluid flow to the electrode assembly 32 can cause point "C" (the vaporisation power threshold) to move to the right in the graph of FIG. 12. The power needed to establish a vapour pocket around the active electrode 34 or 34a is, therefore, increased for a given electrode assembly. Hence, it is desirable to disperse fluid flow for a given electrode assembly, either via the fluid inflow tube 50 or the working channel of the endoscope 68.

Figure 4D:
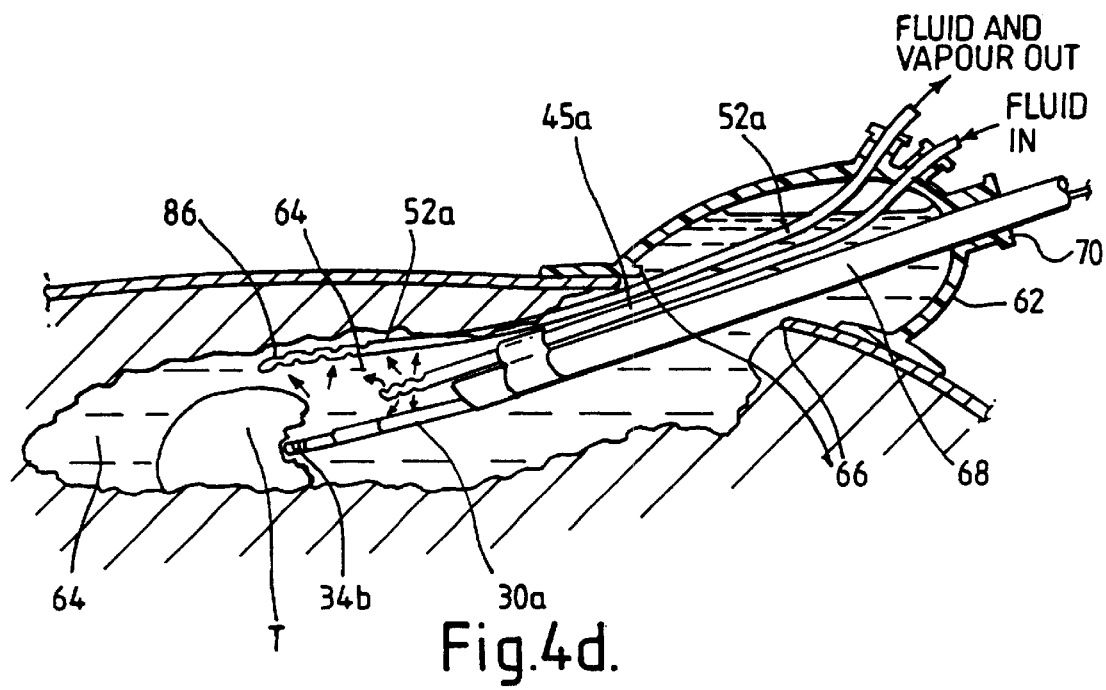

FIGS. 4a to 4d show alternative arrangements for the fluid delivery and outflow tubes. FIGS. 4a and 4b show different terminations for the fluid delivery tube 45 of FIG. 2, these terminations being arranged to dissipate the fluid flow in the vicinity of the operation site, so that the vaporisation power threshold is not significantly increased for a given electrode configuration. In addition to the fluid delivery tube 45 having several inlet apertures 54 as shown in FIG. 2, it could have a single aperture 54a (as shown in FIG. 4a), or it could be a bevelled apertured tube 80 having a distal cage arrangement, the bars 82 of which provide the dispersion of the fluid flow.

FIG. 4c shows a modification of the arrangement shown in FIG. 3, in which fluid delivery is via a fluid delivery tube 45a, rather than being through the endoscope 68, and fluid and/or vapour is removed via a fluid outflow tube 52a. The fluid delivery tube 45a is extended into the surgically-created cavity 64, and is attached by a clip 84, or similar arrangement, to the endoscope 68. Alternatively, this arrangement could be modified when an endoscope is not needed, in which case the tube 45a could be clipped to any other instrument advanced into the cavity 64. The active electrode 34b shown in this embodiment is constituted by a coil structure which is particularly advantageous in vaporising large fleshy lumps of tissues, such as that shown at T.

FIG. 4d shows a modification of the arrangement shown in FIG. 4c, in which the fluid outflow tube 52a is extended into the surgically-created cavity 64, such that vapour and fluid can be extracted from the operation site through apertures 86 in the distal end of the outflow tube. This arrangement is particularly advantageous when working in a horizontal orientation, or when the distal end of the cavity is uppermost, thereby avoiding accumulation of vapour in the cavity.

Figure 5:
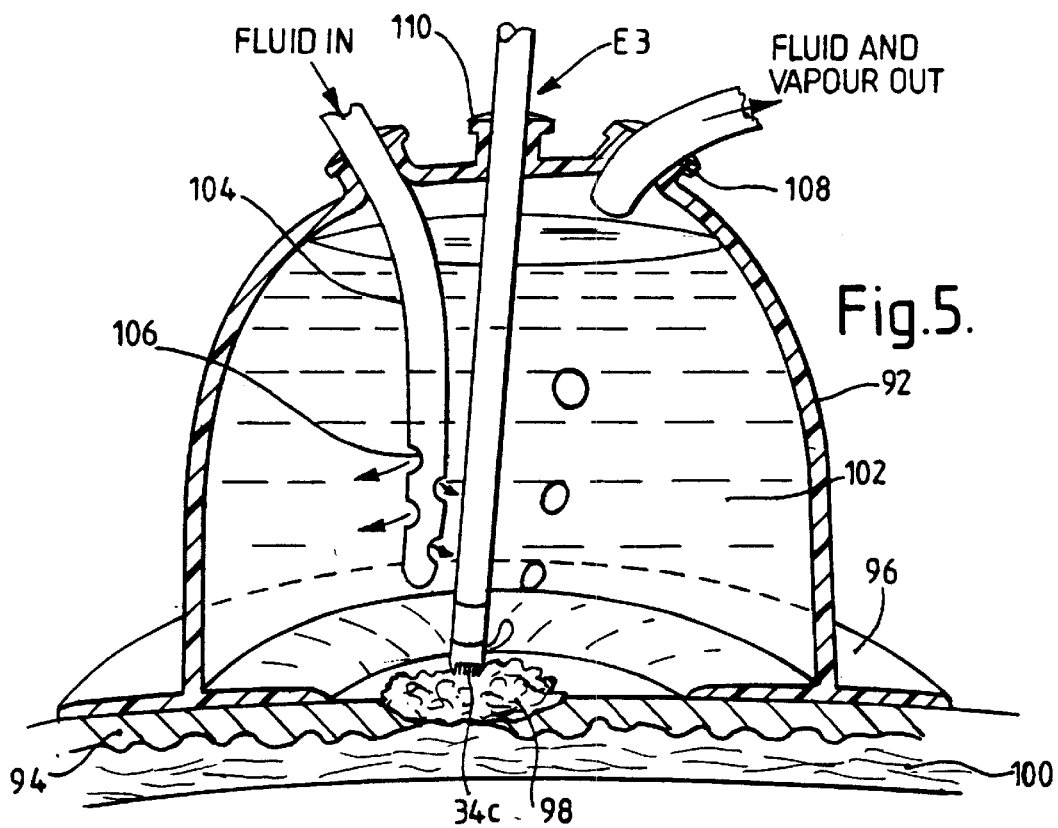
FIGS. 5 to 7 are diagrammatic representations of modified forms of the first embodiment.
Figure 6:
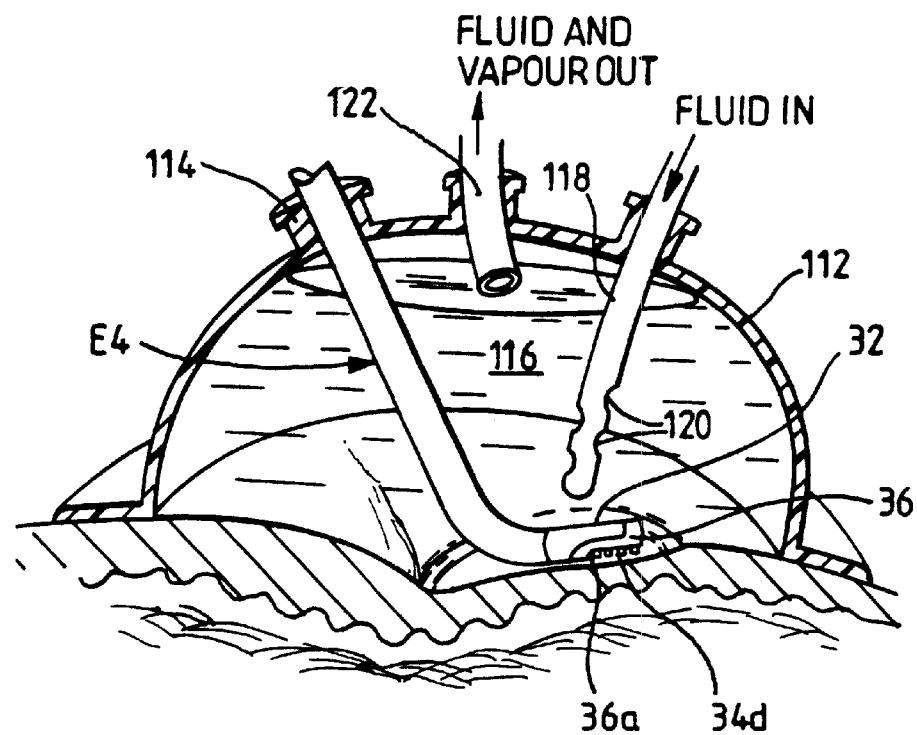
Figure 7:
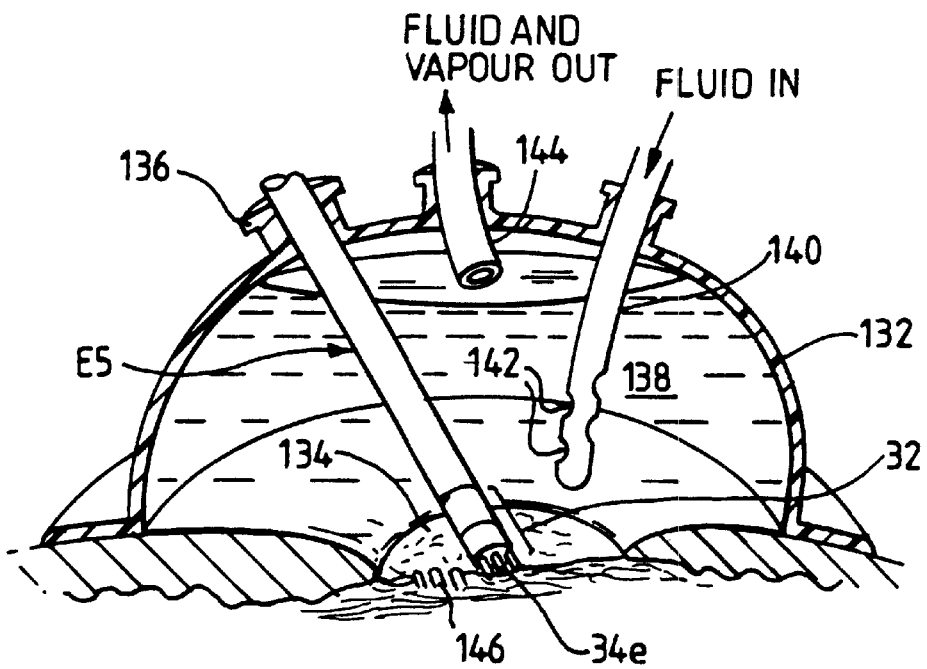

FIGS. 5 to 7 show specific examples of surgical procedures that can be performed with the embodiment of FIG. 2. FIG. 5 shows a cross-section of a modified form of fluid enclosure 92 sealed to the epidermis 94 by a flange 96 formed integrally with the enclosure. The enclosure 92 surrounds a tumour 98 formed in the epidermis 94 above the dermis 100. The tumour 98 is completely immersed in a conductive fluid such as saline 102 which is supplied to the interior of the enclosure 92 via a fluid delivery tube 104, the fluid delivery tube having a plurality of apertures 106 at its distal end. A fluid outflow tube 108 is provided into the top of the enclosure 92 for removal of fluid and/or vapour. An electrosurgical instrument E3 is insertable into the enclosure via a port 110 in the enclosure 92. The electrosurgical instrument E3 is provided with an active electrode 34c in the form of a transverse coil structure. In use, the tumour 98 is progressively removed via vaporisation using the active electrode 34c.

The arrangement shown in FIG. 5 could be modified by incorporating an electrosurgical instrument that can be used to facilitate the excision of a piece of the tumour 98 for hystological examination.

FIG. 6 shows a fluid enclosure 112 which surrounds the surface of skin which is to be contoured during the treatment of superficial skin lesions or for wrinkle removal using the technique of dermabrasion. Here, an electrosurgical instrument E4 is introduced into the enclosure 112 via a port 114. The distal end portion of the instrument E4 is bent substantially at right-angles to the axis of the main body of the instrument, and is provided with a bipolar electrode assembly 32 including an active electrode 34d in the form of a transverse coil. A bipolar electrode assembly incorporating such an active electrode is described in greater detail in the specification of our European patent Application 97926141.9. The active electrode 34d is mounted in a cut-out portion 36a of a ceramic insulator 36, so that it faces laterally with respect to the axis of the distal end portion of the instrument E4. Conductive fluid (such as saline) 116 is introduced into the enclosure 112 via a fluid inflow tube 118 having apertures 120 at its distal end portion. Fluid and/or vapour can leave the enclosure 112 via a fluid outflow tube 122.

FIG. 7 shows a fluid enclosure 132 which surrounds the surface of skin in the region of a chronic ulcerative lesion 134 which is to be treated. An electrosurgical electrode E5 can be inserted into the enclosure 132 via a port 136. A conductive fluid (such as saline) 138 is introduced into the enclosure 132 via a fluid inflow tube 140 having apertures 142 at its distal end. A fluid outflow tube 144 is provided for removing fluid and/or vapour. The electrosurgical instrument E5 includes a bipolar electrode assembly 32 having an active electrode 34e constituted by a plurality of needle filaments. As shown, the active electrode 34e can be used to produce a series of puncture lesions or channels 146 in the chronic ulcerated lesion 134. The aim of creating these lesions 146 is to encourage an angineogenesis such that a more vascular bed is created for grafting or for other corrective techniques. Alternative electrode geometries may be employed to debride such ulcererated lesions, and other surgical procedures will be readily apparent to one skilled in the art.

Figure 9:
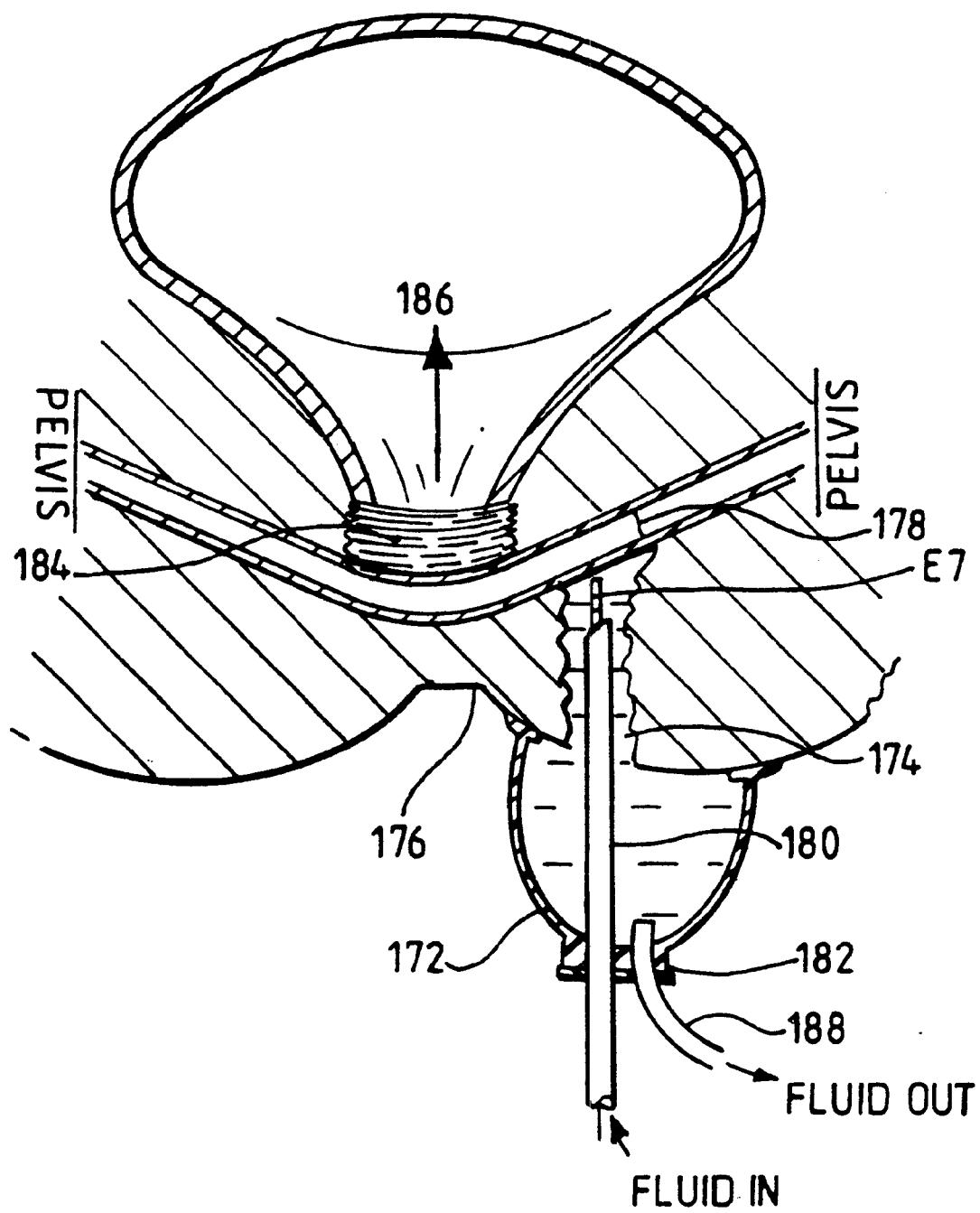

FIGS. 8 and 9 show specific examples of surgical procedures that can be performed with the embodiment of FIG. 3, that is say where a surgically-created cavity 64 surrounds the operation site. FIG. 8 shows a fluid enclosure 152 surrounding an incision 66 leading to the cavity 64. The figure shows the dermal layer 154 of the skin being accessed through a subcutaneous tunnel 156 to facilitate thermal modification of collagen fibres. An electrosurgical instrument E6 is introduced into the tunnel 156 through the fluid enclosure 152, the instrument having a distal end portion which is bent substantially at right-angles to the axis of the main body of the instrument, and being provided with an active electrode 34f in the form of a transverse coil structure. The shaft of the instrument E6 is malleable to allow application of the active electrode 34f to the deep side of the dermis 154. A conductive fluid (such as saline) 158 is introduced through the fluid enclosure 152 to the operation site via a fluid inflow tube 158 having apertures 160 at its distal end. A fluid outflow tube 162 is also provided. The instrument E6 can be used for thermal modification by application of the active electrode 34f by activating the generator 1 (not shown in this figure) in the desiccate mode.

FIG. 9 shows a fluid enclosure 172 which surrounds a surgically-created cavity 174 through the perineum 176 to access the urogenital diaphragm and pelvic floor 178. In this embodiment, an endoscope 180 is used to guide an electrosurgical instrument E7 into the cavity 174. The endoscope 180 is inserted through a port 182 provided in the fluid enclosure 172, with the patient typically being placed in the lithotomy position. The pelvic floor 178, and other collagen containing fascial structures, can be modified (tightened) using the electrode structure of the instrument E7 in combination with the desiccate output from the generator 1 (not shown in FIG. 9) in the treatment of stress urinary incontinence of the female by correction of bladder neck descent. The surgical space can be extended both anteriorly and posteriorly to provide a uniform modification of the structures such that the bladder neck 184 is elevated in the direction 186. Similarly, tendinous structures associated with muscle insertions to bone, joint support structures or ligaments of the body can be treated following repetitive strain injuries, degenerative changes or other injuries, as exemplified by the arrangements shown in FIG. 10. Conductive fluid (such as saline) is supplied to the operation site via the fluid enclosure 172 through the interior channel of the endoscope 180. Fluid leaves the enclosure 172 via a fluid outflow tube 188.

FIG. 10 illustrates a modified form of fluid enclosure 192 constituted by a generally tubular member provided with a sealing flange 194. An inflatable balloon 196 is mounted on the fluid enclosure 192, and can be used to apply pressure between the surface 198 of the skin and the sealing flange 194. A ligamentous structure 200 (such as the lateral ligament of the knee) of the patient's body can be treated by an electrosurgical instrument E8 which is introduced into a surgically-created cavity 64 adjacent thereto via an endoscope 202. Conductive fluid (such as saline), is introduced into the cavity 64 through the working channel of the endoscope 202. An endoscope/instrument and fluid management port 204 is provided, and this may also include fluid delivery channels. Fluid is removed via a fluid outflow tube 206 mounted in the port 204. In use, the balloon 196 is inflated with liquid or gas, once the device is positioned through an incision 208 in the skin 198, using an inflation tube (not shown). Alternatively, the sealing flange 194 may constitute a second balloon for sealing around the aperture to the surgical cavity 64. The electrosurgical instrument E8 includes an active electrode 34g having a coiled structure.

Figure 11:
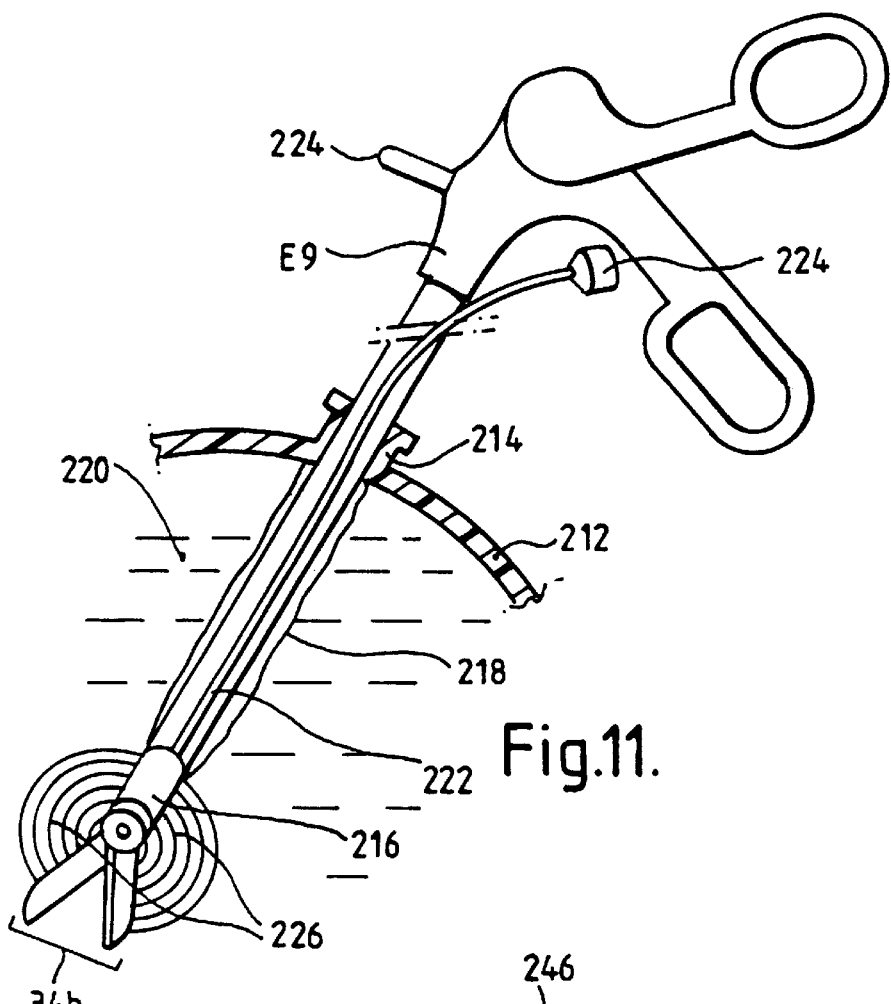
FIG. 11 is a diagrammatic representation of a further modification for use with either the first embodiment or the second embodiment.

FIG. 11 illustrates a means of using the invention with a conventional monopolar electrosurgical instrument, such as that shown at E9. The instrument E9 can be inserted through a port 214 in a fluid enclosure 212. The instrument E9 of this embodiment can be used for surgical procedures on the skin surface or in artificially-created cavities within the patient's body. Accordingly, the enclosure 212 (part only of which is shown in FIG. 11) could be of any of the types previously described. However, even though the instrument E9 is itself a monopolar instrument, it is used in a bipolar configuration by providing a return electrode 216 mounted at the distal end of a thin sleeve 218 which is fixed to the shaft of the instrument so that a fixed relationship is maintained between the return electrode and the active electrode 34h, which here is constituted by a scissors arrangement. Conductive fluid (such as saline) 220 is introduced into the enclosure 212 by a fluid inflow tube (not shown). Similarly, a fluid outflow tube (not shown) is provided for removal of conductive fluid 220. The return electrode 216 is electrically connected by a cord 222 and a connector 224 to one side of the bipolar electrosurgical output of the generator 1 (not shown in this figure). A monopolar connector post 224 of the instrument E9 is connected to the other side of the generator. In use, the generator can be energised in the desiccation mode to create an electric field pattern 226 so that the active electrode 34h can be used for coagulation or desiccation of tissue in a bipolar mode. The vaporising or cutting output of the generator cannot be used in this embodiment.

Another new aspect to the invention is the use of a fluid outflow tube with a floating tip, as shown in FIGS. 13a to 13d. In each of these figures, a fluid enclosure 232 includes a fluid outflow tube 234, the tip 234a of which is made of, or incorporates, buoyancy material, so that the tip floats within electrically-conductive fluid (such as saline) 236 within the enclosure, with the tube inlet within the "air space" at the top of the enclosure. In this way the tip floats to areas where gases produced by vaporisation are easily removed.

Figure 14:
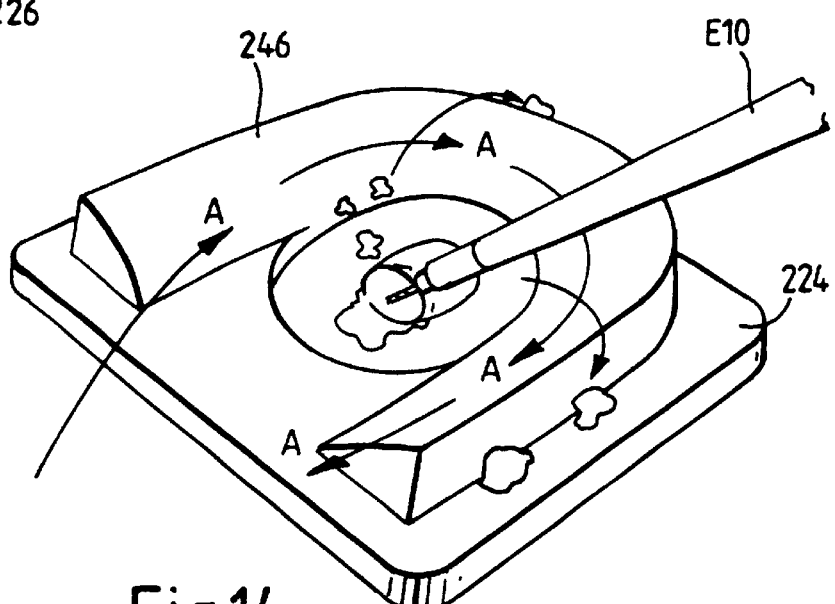
FIG. 14 shows a further modified arrangement.

Another new aspect of the invention (shown in FIG. 14) is that, by using a fluid inflow tube (not shown) at a tangent to a fluid enclosure (only the base 244 of which is shown), a rotating fluid current can be generated. This rotating current, indicated by the arrows A, causes tissue debris produced by an electrosurgical instrument E10 to be thrown outwardly away from the central treatment region. The base 244 of the enclosure is constructed in such a way to trap this debris. The enclosure base 244 incorporates a ridge 246 to capture debris and prevent it from returning to the operative site.

In order to facilitate visualisation of an operation site, each of the fluid enclosures 42, 62, 92, 112, 132, 152, 172, 192, 212 and 222 could be made of translucent or transparent material.

It will be apparent that modifications could be made to the embodiments described above. In particular, each of the fluid enclosures could include a gas-permeable membrane portion to allow vaporised tissue to escape therefrom. Also, thermal protection means could be incorporated into the fluid enclosure to prevent elevated temperatures as a result of power flow.

What is claimed is:

1. An electrosurgical system comprising a radio frequency generator, an electrosurgical instrument, and a fluid enclosure, the generator having a radio frequency output for delivery of power to the electrosurgical instrument when immersed in an electrically-conductive fluid, the electrosurgical instrument having an electrode assembly at the distal end thereof, the electrode assembly comprising a tissue treatment electrode, and a return electrode axially spaced therefrom in such a manner as to define, in use, a conductive fluid path that completes an electrical circuit between the tissue treatment electrode and the return electrode, wherein the fluid enclosure is adapted to surround an operation site on the skin of a patient or an incision leading to a cavity surgically created within the patient's body, wherein the fluid enclosure includes sealing means for sealing against the patient's tissue, and wherein the fluid enclosure includes at least one port through which the electrosurgical instrument is insertable, and through which the electrically-conductive fluid can enter and/or leave the enclosure.

2. An electrosurgical system as claimed in claim 1, wherein the fluid enclosure is provided with an inlet through which the electrosurgical instrument can be inserted.

3. An electrosurgical instrument as claimed in claim 1, wherein the fluid enclosure is provided with port means for supplying electrically-conductive fluid to, and removing said fluid from, the fluid enclosure.

4. A system as claimed in claim 3, wherein the fluid enclosure is provided with a fluid inflow tube and a fluid outflow tube, each of which is associated with a respective port in the fluid enclosure.

5. A system as claimed in claim 4, wherein the fluid inflow tube is provided with a plurality of apertures at the distal end portion thereof.

6. A system as claimed in claim 2, wherein the inlet is adapted to receive an endoscope, the electrosurgical instrument being insertable, in use, through the endoscope.

7. A system as claimed in claim 6, wherein the fluid enclosure is provided with a port through which electrically-conductive fluid can be removed from the enclosure, a working channel within the endoscope constituting a channel for delivering electrically-conductive fluid to the interior of the fluid enclosure.

8. A system as claimed in claim 2, wherein the fluid enclosure is provided with a window, through which a surgeon can visualise the region surrounding the tissue treatment electrode.

9. A system as claimed in claim 8, wherein the window is a magnifying window.

10. A system as claimed in claim 1, wherein the electrosurgical instrument is a monopolar instrument having a single, tissue treatment electrode at the distal end thereof, and a metal collar positioned, in use, adjacent to the tissue treatment electrode constitutes the return electrode, the metal collar and the tissue treatment electrode being connected to the generator.

11. A system as claimed in claim 1, wherein the fluid enclosure is such that it covers an area of skin surrounding the operation site or incision that is substantially larger than the area of the operation site or incision, whereby the volume of electrically-conductive fluid contained in the fluid enclosure is sufficiently large to ensure that its heat capacity is effective to remove heat away from tissue-being treated.

12. A system as claimed in claim 1, wherein the sealing means is constituted by an outwardly-extending flange provided on the fluid enclosure.

13. A system as claimed in claim 12, wherein the flange is integrally formed with the fluid enclosure.

14. A fluid enclosure device for use in electrosurgical procedures, the device comprising:
 a translucent flexible web member having a sealing flange at its periphery for forming a substantially fluid-tight seal with a patient's skin thereby to enable tissue to be treated within a substantially fluid-tight enclosure provided by the patient's skin and the flexible web member,
 a first aperture in the web member to enable introduction of an electrosurgical instrument into the enclosure while maintaining integrity of the substantially fluid-tight seal,
 a second aperture to enable supply of electrically-conductive fluid within the enclosure,
 a third aperture to enable removal of waste matter from within the enclosure, and
 a fluid outflow tube extending from the third aperture into the enclosure, the outflow tube being buoyant in electrically-conductive liquid.

15. A method of treating tissue using an electrosurgical system comprising an electrosurgical generator adapted to generate a radio frequency oscillating voltage output across first and second output terminals; an electrosurgical instrument having an active tissue treatment electrode connected to the first generator output terminal; fluid delivery means for delivering electrically-conductive fluid to the tissue to be treated; and a return electrode connected to the second generator output terminal, the method comprising the steps of:
 enclosing, in a substantially fluid-tight manner, a space within which the tissue to be treated is located, and within which at least the active electrode is located;
 operating the fluid delivery means at least partly to fill the space with electrically-conductive fluid;
 operating the generator to apply a radio frequency voltage between the active and return electrodes, and completing at least a part of a conduction path between the active and return electrodes using the electrically-conductive fluid; and
 manipulating the active electrode in the vicinity of the tissue to be treated.

16. A method according to claim 15, further comprising the step of positioning the return electrode within the space.

17. A method according to claim 15, wherein the electrosurgical instrument comprises a shaft, and the active and return electrodes are located on a distal end of the shaft, the method further comprising the steps of positioning the proximal end of the shaft to extend out of the space, and manipulating the active electrode by moving the proximal end of the shaft.

18. A method according to claim 15, wherein the electrically-conductive fluid is supplied to the space continually, and the method further comprises the step of removing waste matter from within the space.

19. A method according to claim 15, wherein the space is enclosed by means of a flexible enclosing member which forms a seal with a patient's skin, and the method further comprises the step of reducing the pressure within the space to a level below air pressure in the immediate vicinity outside the space.

20. A method according to claim 15, wherein the space is enclosed by means of a flexible enclosing member which forms a seal with a patient's skin, and the method further comprises the step of adhesively fixing the flexible member to the patient's skin.

21. A method according to claim 15, wherein the enclosing step is such that the space encloses a region of the epidermis.

22. A method according to claim 21, wherein the active electrode is manipulated to achieve at least one of the following: treatment of skin lesions; removal of tumours; dermabrasion; reduction of wrinkles; removal of wrinkles; treatment of solar keratosis, treatment of basal cell carcinoma.

23. A method according to claim 15, wherein the enclosing step is such that the space encloses a cavity within which the tissue to be treated is situated.

24. A method according to claim 23, wherein the cavity is a natural body cavity.

25. A method according to claim 23, wherein the active electrode is manipulated to achieve at least one of the following: thermal modification of collagen fibres; treatment of parenchymal and mesanchymal tumours.

26. A method according to claim 25, wherein the thermal modification of collagen fibres is performed to correct bladder neck descent.

27. A method according to claim 25, wherein the thermal modification of collagen fibres is performed to treat ligaments or tendons.

* * * * *